United States Patent
Nieves (10) Patent No.: US 9,390,676 B2
(45) Date of Patent: Jul. 12, 2016

(54) TACTILE PRESENTATION OF INFORMATION

(75) Inventor: Johnny Nieves, Yonkers, NY (US)

(73) Assignee: International Business Machines Corporation, Armonk, NY (US)

( * ) Notice: Subject to any disclaimer, the term of this patent is extended or adjusted under 35 U.S.C. 154(b) by 977 days.

(21) Appl. No.: 13/238,552

(22) Filed: Sep. 21, 2011

(65) Prior Publication Data

US 2013/0073954 A1 Mar. 21, 2013

(51) Int. Cl.
| | |
|---|---|
| G06F 3/01 | (2006.01) |
| G09G 3/38 | (2006.01) |
| G06F 1/16 | (2006.01) |
| G09B 21/00 | (2006.01) |
| G06F 3/14 | (2006.01) |
| G09G 3/20 | (2006.01) |

(52) U.S. Cl.
CPC ............... *G09G 3/38* (2013.01); *G06F 1/1637* (2013.01); *G06F 3/016* (2013.01); *G06F 3/14* (2013.01); *G09B 21/004* (2013.01); *G09G 3/2003* (2013.01); *G09G 2300/02* (2013.01); *G09G 2300/0452* (2013.01); *G09G 2300/0469* (2013.01); *G09G 2310/027* (2013.01); *G09G 2310/0272* (2013.01); *G09G 2370/02* (2013.01)

(58) Field of Classification Search
CPC .......... G06F 3/01; G09B 21/02; G09B 21/00; G01R 3/00; G08B 5/22; G09G 5/00; G09G 3/00
See application file for complete search history.

(56) References Cited

U.S. PATENT DOCUMENTS

| | | | |
|---|---|---|---|
| 4,516,189 | A | 5/1985 | Seaks, Jr. |
| 5,176,528 | A | 1/1993 | Fry et al. |
| 5,222,895 | A | 6/1993 | Fricke |
| 5,244,288 | A | 9/1993 | Nagaoka et al. |

(Continued)

FOREIGN PATENT DOCUMENTS

| | | |
|---|---|---|
| CN | 101133432 A | 2/2008 |
| CN | 101965500 A | 2/2011 |

(Continued)

OTHER PUBLICATIONS

Braille Technology, "Features and Functions of the Braille PDA," retrieved from: http://www.nbp.org/icinbp/technology/braillepdafeatures.html?id-tw9to6kh on Sep. 16, 2011, 1 page.

(Continued)

*Primary Examiner* — Tony N Ngo
(74) *Attorney, Agent, or Firm* — Dan Simek; Hoffman Warnick LLC (57) ABSTRACT

Embodiments of the invention provide a device and system for providing information to a user in a tactile form. In one embodiment, the invention provides a device for providing information to a user, the device comprising: a plurality of individually-addressable cells, each cell including an electrically-active material capable of changing shape and/or position in response to an electrical current; a electrical network connected to, and capable of delivering the electrical current to, each of the plurality of individually-addressable cells; a membrane atop the plurality of individually-addressable cells, onto which the change in shape and/or position of the electrically-active material in each cell may be transferred; and a receiver for receiving information capable of tactile presentation to a user using the plurality of individually-addressable cells.

18 Claims, 6 Drawing Sheets

(56) References Cited

U.S. PATENT DOCUMENTS

| | | |
|---|---|---|
| 5,496,174 A | 3/1996 | Garner |
| 5,629,831 A | 5/1997 | Eggert et al. |
| 5,766,013 A | 6/1998 | Vuyk |
| 6,417,821 B1 | 7/2002 | Becker et al. |
| 6,449,732 B1 | 9/2002 | Rasmussen et al. |
| 6,502,032 B1 | 12/2002 | Newman |
| 6,547,569 B1 | 4/2003 | Issan |
| 6,743,021 B2 | 6/2004 | Prince et al. |
| 6,881,063 B2 | 4/2005 | Yang |
| 6,942,785 B2 | 9/2005 | Bayer et al. |
| 6,988,221 B2 | 1/2006 | Rasmussen et al. |
| 7,009,595 B2 | 3/2006 | Roberts et al. |
| 7,099,152 B2 | 8/2006 | Gasbarro et al. |
| 7,382,357 B2 | 6/2008 | Panotopoulos et al. |
| 7,436,318 B2 | 10/2008 | Affolter et al. |
| 7,797,558 B2 | 9/2010 | Ghoshal |
| 8,301,237 B2 | 10/2012 | Lanfermann et al. |
| 8,451,240 B2 | 5/2013 | Pasquero et al. |
| 8,456,438 B2 | 6/2013 | Ciesla et al. |
| 8,668,514 B2 | 3/2014 | Morosi et al. |
| 2002/0090846 A1 | 7/2002 | Abboud |
| 2002/0106614 A1* | 8/2002 | Prince et al. .................. 434/114 |
| 2003/0141504 A1 | 7/2003 | Kuwabara et al. |
| 2004/0031767 A1 | 2/2004 | Ice |
| 2005/0030292 A1 | 2/2005 | Diederiks |
| 2005/0057528 A1 | 3/2005 | Kleen |
| 2005/0182389 A1 | 8/2005 | LaPorte et al. |
| 2007/0152982 A1 | 7/2007 | Kim et al. |
| 2008/0109677 A1 | 5/2008 | Rasmussen et al. |
| 2008/0138774 A1* | 6/2008 | Ahn et al. ..................... 434/114 |
| 2008/0206722 A1* | 8/2008 | Fukami ......................... 434/114 |
| 2008/0303796 A1 | 12/2008 | Fyke |
| 2009/0171233 A1 | 7/2009 | Lanfermann et al. |
| 2009/0177385 A1* | 7/2009 | Matas et al. .................. 701/209 |
| 2009/0194226 A1 | 8/2009 | Tabet |
| 2010/0079410 A1 | 4/2010 | Minton |
| 2010/0225456 A1 | 9/2010 | Eldering |
| 2010/0303733 A1* | 12/2010 | Hyde et al. ................. 424/9.341 |
| 2012/0235935 A1 | 9/2012 | Ciesla et al. |
| 2013/0073954 A1 | 3/2013 | Nieves |
| 2013/0084730 A1 | 4/2013 | Morosi et al. |
| 2013/0142367 A1 | 6/2013 | Berry et al. |
| 2014/0016253 A1 | 1/2014 | Lee et al. |
| 2014/0272781 A1 | 9/2014 | Mohan et al. |
| 2014/0288666 A1 | 9/2014 | Gill |
| 2015/0199937 A1 | 7/2015 | Blumert et al. |

FOREIGN PATENT DOCUMENTS

| | | |
|---|---|---|
| DE | 102007054888 A1 | 5/2009 |
| EP | 0585548 A1 | 3/1994 |
| FR | 2876011 A1 | 4/2006 |
| JP | H01158629 A | 6/1989 |
| JP | 2000148393 A | 5/2000 |
| JP | 2005202545 A | 7/2005 |
| JP | 2006246108 A | 9/2006 |
| JP | 2007079172 A | 3/2007 |
| JP | 2008209793 A | 9/2008 |
| JP | 2010532043 A | 9/2010 |
| KR | 20080051997 A | 6/2008 |
| KR | 20100117067 A | 11/2010 |
| TW | 201028298 A | 8/2010 |
| WO | 2011018728 A1 | 2/2011 |

OTHER PUBLICATIONS

Patent Cooperation Treaty, International Search Report for PCT/CN2012/081043 mailed on Dec. 6, 2012, 4 pages.

Patent Cooperation Treaty, Written Opinion of the International Searching Authority for PCT/CN2012/081043 mailed on Dec. 6, 2012, 5 pages.

Abbott et al., "Virtual I/O Server Deployment Examples," IBM Advanced Power Virtualization on IBM System Redpaper, retrieved from www.ibm.com/redp4224/redpaper/, Feb. 2007, 96 pages.

Hughes, et al., "BladeCenter midplane and media interface card," Nov. 2005, pp. 823-836, IBM Journal of Research and Development, vol. 49, No. 6.

T.A.C. Schneider Electric, "NetContoller II—CPU Module," Jun. 2008, 4 pages, retrieved from www.tac.com/NetControllerII.

Andover Controls "Andover Continuum-NetController II CPU Module," 2000, 6 pages, retrieved from http://us.sourcesecurity.comidatasheets/tac-netcontroller/co-1995-ga/netcontroller.pdf.

The Telegraph, "Man gets smartphone dock built into prosthetic arm," Oct. 2011, 2 pages, retrieved from http://www.telegraph.co.uk/technology/news/8848476/Man-gets-smartphone-dock-built-into-prosthetic-arm.html.

Hanlon, "Touch Messenger sends and receives text messages in Braille," Jul. 2006, 4 pages, http://www.gizmag.com/go/5876.

United States Access Board, "Advancing Full Access and Inclusion for All," No date available, retrieved from https://www.access-board.gov/, 3 pages.

Braille Street Sign, No Date, 1 page, retrieved from http://www.walkinginfo.org/.

Science Direct, "Keep up to date on newly-published research with the Research Highlights app," Copyright 2014 Elsevier B.V., 3 pages, http://www.sciencedirect.com/science.

NBP—Technology: Braille PDA, national: braille technology, print date Sep. 16, 2011, 1 page, www.nbp.org/ic/nbp/ technology/braillepdafeatures.

\* cited by examiner

TACTILE PRESENTATION OF INFORMATION

BACKGROUND

The present invention relates generally to devices and systems for the delivery of information and, more particularly, to devices and systems for the presentation of information to a user in a tactile form.

Advances in technology, particularly in the area of communications technology, have provided users with a wealth of devices and systems for the exchange of information. However, virtually all such devices and systems are visually-based, requiring a user to visualize some portion of the device in order to take advantage of its capabilities. This leaves a significant portion of the population, the visually impaired, without the ability to take advantage of these devices and systems.

BRIEF SUMMARY

Embodiments of the invention provide a device and system for providing information to a user in a tactile form.

A first aspect of the invention provides a device for providing information to a user, the device comprising: a plurality of individually-addressable cells, each cell including an electrically-active material capable of changing shape and/or position in response to an electrical current; a electrical network connected to, and capable of delivering the electrical current to, each of the plurality of individually-addressable cells; a membrane atop the plurality of individually-addressable cells, onto which the change in shape and/or position of the electrically-active material in each cell may be transferred; and a receiver for receiving information capable of tactile presentation to a user using the plurality of individually-addressable cells.

A second aspect of the invention provides a system for providing information to a user, the system comprising: a device including: a plurality of individually-addressable cells, each cell including an electrically-active material capable of changing shape and/or position in response to an electrical current; a electrical network connected to, and capable of delivering the electrical current to, each of the plurality of individually-addressable cells; a membrane atop the plurality of individually-addressable cells, onto which the change in shape and/or position of the electrically-active material in each cell may be transferred; and a receiver for receiving information capable of tactile presentation to a user using the plurality of individually-addressable cells; and a transmitter for transmitting to the device the information capable of tactile presentation.

The illustrative aspects of the present invention are designed to solve the problems herein described and other problems not discussed, which are discoverable by a skilled artisan.

BRIEF DESCRIPTION OF THE SEVERAL VIEWS OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not to scale. The drawings are intended to depict only typical aspects of the invention, and therefore should not be considered as limiting the scope of the invention. In the drawings, like numbering represents like elements among the drawings.

DETAILED DESCRIPTION

Figure 1:
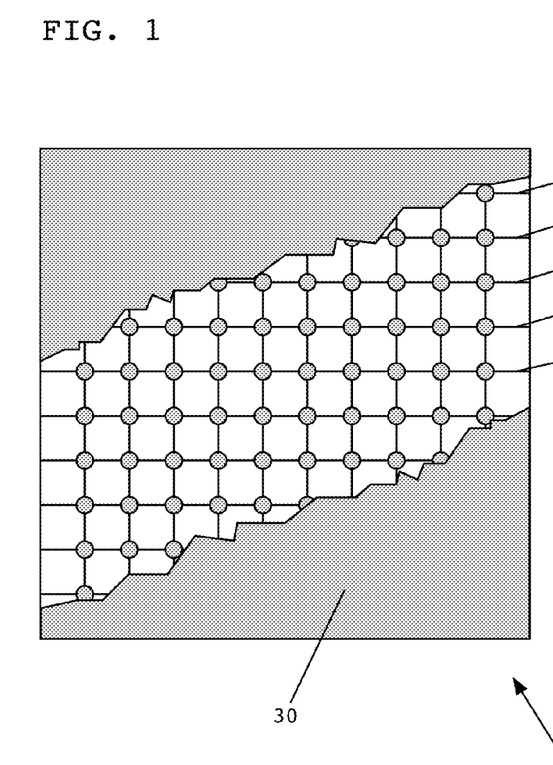
FIGS. 1 and 2 show a schematic top view of a device according to one embodiment of the invention.
Figure 2:
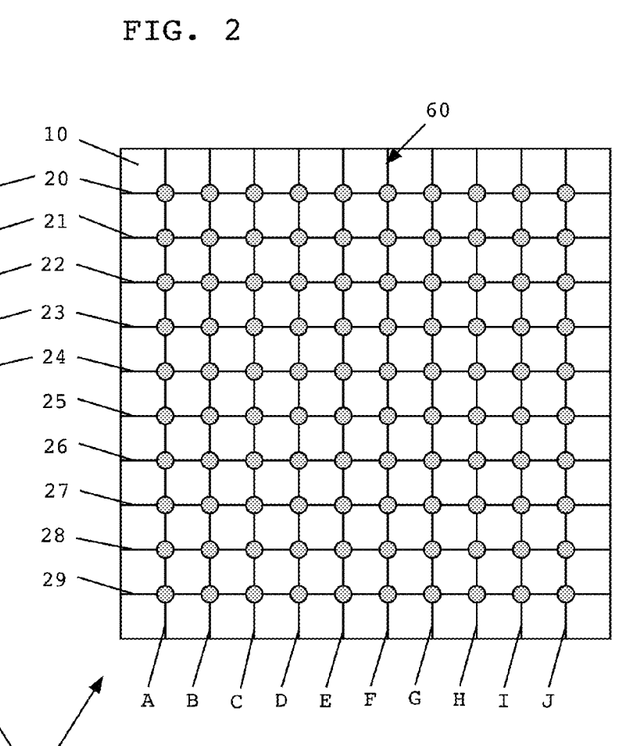

Referring now to the drawings, FIGS. 1 and 2 show schematic views of a portion of a device 100 capable of presenting information to a user in a tactile form. Device 100 includes a substrate 10 into which is formed a plurality of cells arranged in an array of rows 20-29 and columns A-J and connected to an electrical network 60 capable of delivering an electrical current independently to each of the plurality of cells.

In FIG. 1, a flexible membrane 30 (shown in partial cutaway) is laid atop substrate 10 and the plurality of cells. For purposes of explanation, membrane 30 is not shown in FIG. 2. Each of the plurality of cells is individually-addressable by the electrical network 60 and includes an electrically-active material capable of changing shape and/or position in response to an electrical current. Such change in shape and/or position is transferred to an underside of membrane 30 and, due to the flexibility of membrane 30, to a top surface of membrane 30.

Membrane 30 may include any known or later-developed material capable of transferring to a top surface the change in shape and/or position imposed upon its underside. Suitable materials include, but are not limited to, silicone materials and rubber materials.

Figure 3:
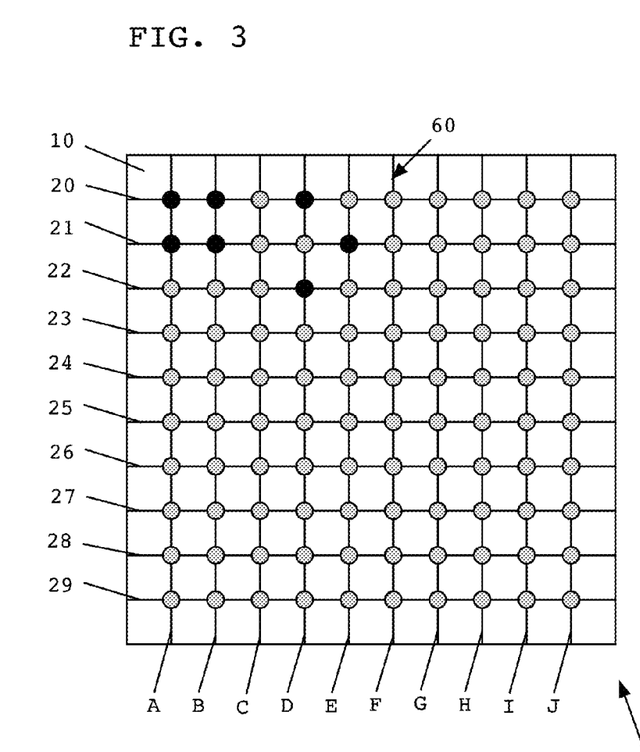
FIGS. 3 and 4 show the device of FIGS. 1 and 2 while displaying Braille characters.
Figure 4:
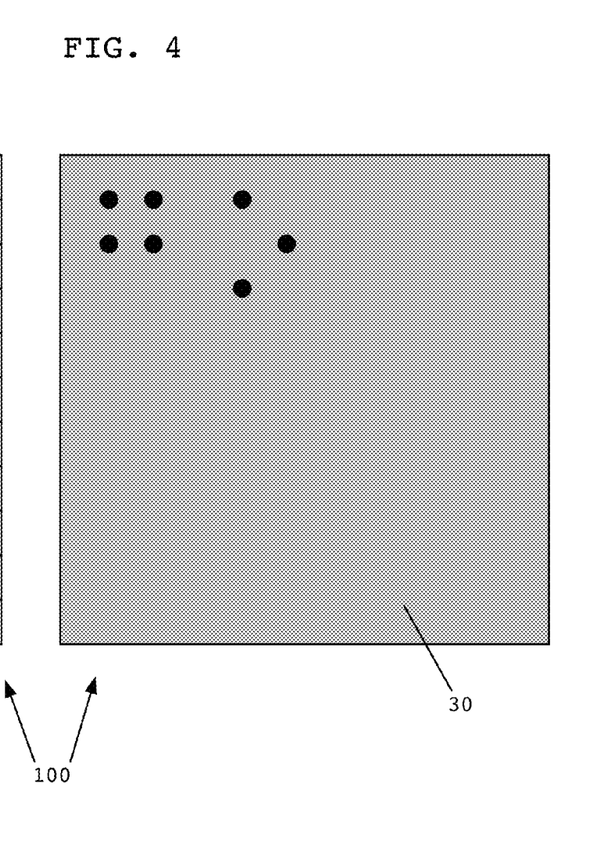

FIG. 3, for example, shows device 100, in which cells 20A (i.e., row 20, column A), 20B, 21A, and 21B, as well as cells 20D, 21E, and 22D, have been electrically activated to induce a change in shape and/or position of an electrically-active material therein. FIG. 4 shows device 100 with membrane 30 in place, such that electrically activated cells 20A, 20B, 21A, and 21B form the Braille character "G" and electrically activated cells 20D, 21E, and 22D form the Braille character "O" on a top surface of membrane 30.

Figure 5:
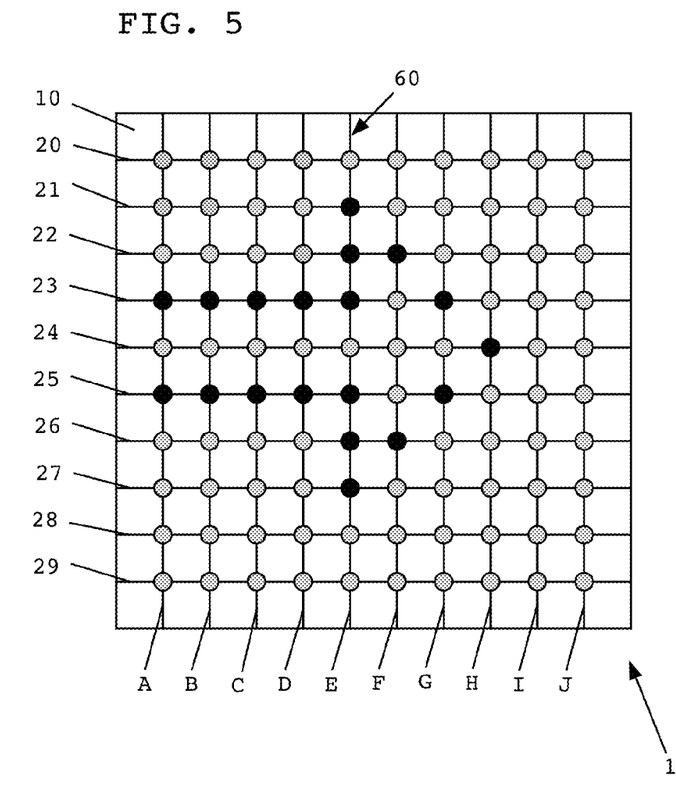
FIGS. 5 and 6 show the device of FIGS. 1 and 2 while displaying a navigational symbol.
Figure 6:
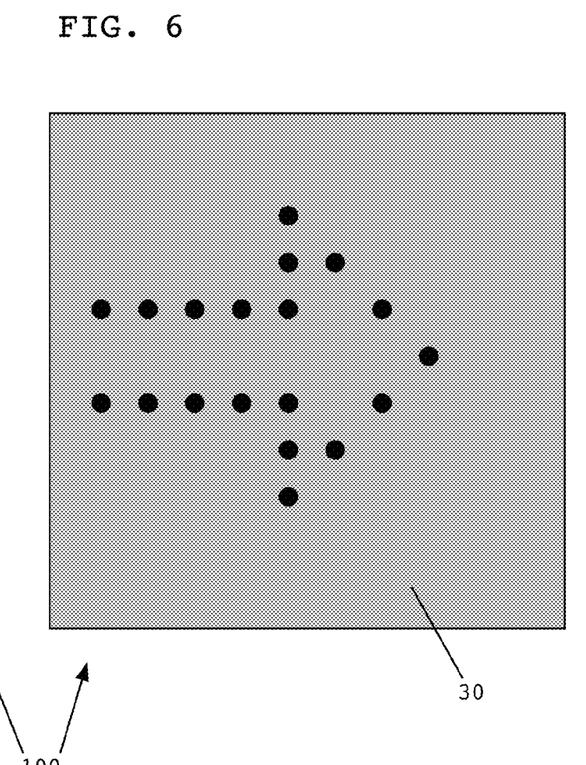

Braille characters, however, are not the only forms of tactile information that may be provided using device 100. For example, FIGS. 5 and 6 show the representation of a navigational symbol, an arrow. In FIG. 5, cells 21E, 22E, 22F, 23A, 23B, 23C, 23D, 23E, 23G, 24H, 25A, 25B, 25C, 25D, 25E, 25G, 26E, 26F, and 27E have been electrically activated. In FIG. 6, which shows membrane 30 in place, an arrow symbol is displayed due to the electrical activation of the cells shown in FIG. 5.

In some embodiments of the invention, device 100 may include other components for facilitating the presentation of information to a user. For example, device 100 may include a receiver capable of receiving information contained in one or more formats, such as a text message, an electronic mail message, a voicemail message, or a navigational instruction.

In other embodiments of the invention, device 100 may include a global positioning system (GPS) component for determining a position of device 100. This may be particularly beneficial, for example, where device 100 is used to relay navigational and/or positional information to a user.

While FIGS. 1 through 6 show the cells of device 100 arranged in an array of rows and columns, this is not necessary or essential. Other arrangements of cells are possible, as will be apparent to one skilled in the art, and are within the scope of the invention. The evenly-distributed arrangement of cells shown in FIGS. 1 through 6 is merely illustrative, although such arrangements are advantageous for the representation of Braille characters, etc., which themselves are based on components distributed across evenly-distributed rows and columns.

Figure 7:
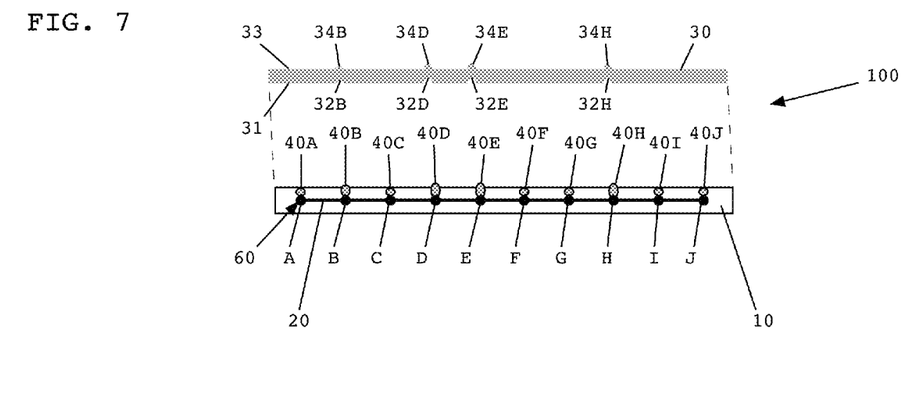
FIG. 7 shows a side cross-sectional view of the device of FIG. 2.

FIG. 7 shows a side cross-sectional view through row 20 of device 100. Here, membrane 30 is shown raised above substrate 10 for purposes of explanation and illustration. In use, membrane 30 would lie atop substrate 10, as described above.

As can be seen in FIG. 7, an electrically-active material 40A-J is shown within substrate 10 and in communication with electrical network 60. The electrically-active material 40A-J of each cell is capable of changing shape and/or position in response to an electrical current supplied by electrical network 60. For example, electrically-active material, in some embodiments, may include a quantity of a polar material that, in the absence of an electrical current is electrically neutral, but which may adopt a change in shape and/or position in response to a supplied electrical current. Some oils, for example, are capable of adopting a changed shape in response to an electrical current, with the electrons of the individual oil molecules attracted toward a positive electrical current supplied by electrical network 60 and the positively charged nuclei of the individual oil molecules being repelled away from the positive electrical current.

In some embodiments of the invention, a solid electrically-active material is employed. Suitable materials include, for example, alloys of samarium and cobalt. Other materials will be apparent to one skilled in the art and are within the scope of the invention. Regardless of the electrically-active material employed, the result is a change in shape and/or position of the electrically-active material within the cell, such that an impression 32B, 32D, 32E, 32H is made on an underside 31 of membrane 30 which, due to the flexible nature of membrane 30, is transferred to a surface 33 of membrane 30 as raised features 34B, 34D, 34E, 34H.

Figure 8:
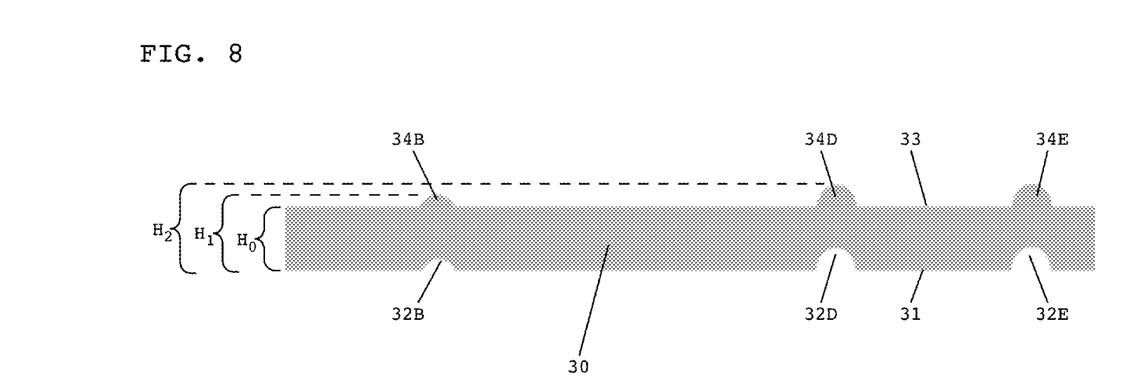
FIG. 8 shows a detailed side cross-sectional view of a portion of the device of FIG. 7.

FIG. 8 shows a detailed view of a portion of membrane 30 of FIG. 7. As can be seen in FIG. 8, raised features of varying heights may be transferred to surface 33 of membrane 30 by varying the degree or extent of change in shape and/or position of the electrically-active material beneath. This varying degree or extent of change in shape and/or position, in turn, may be achieved, for example, by altering a current to which the electrically-active material is exposed. The consequence of this varying degree or extent of change in shape and/or position is a membrane capable of providing a user with a contoured or multi-level display of tactile information.

For example, in FIG. 8, cells which have not been electrically activated result in an unraised, H0, surface 33 of membrane 30. Other cells, which have been activated, result in raised features 34B having a first height H1 greater than the unraised, H0, surface 33. Still other cells have been activated to a greater degree or extent, resulting in raised features 34D, 34E having a second height H2 greater than the first height H1 and the unraised, H0, surface 33. While membrane 30 is shown in FIG. 8 as including raised features 34B, 34D, 34E capable of producing a surface 33 having three heights, it should be understood that this is merely for purposes of illustration and that any number of levels may be achieved, as may a continuum of raised feature heights.

Figure 9:
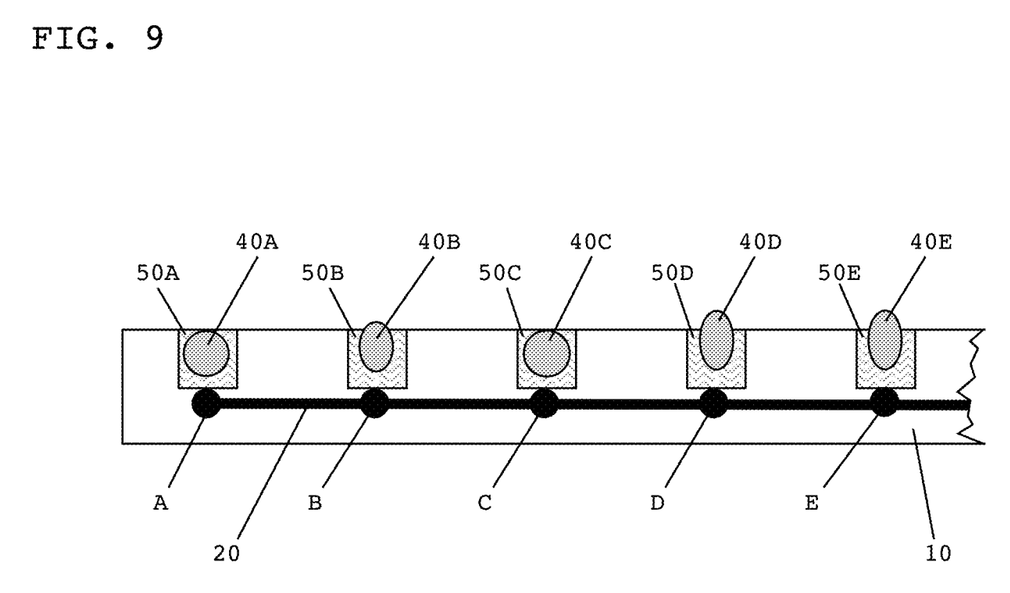
FIG. 9 shows a detailed side cross-sectional view of another portion of the device of FIG. 7.

FIG. 9 shows a detailed view of a portion of substrate 10 of FIG. 7. In FIG. 9, individual cells 50A-50E may be seen within substrate 10, each containing an electrically-active material 40A-E. In some embodiments of the invention, each cell 50A-E may include a support material, such as a fluid, which may ease or facilitate changes in shape and/or position of the electrically-active material 40A-E.

While the embodiments of FIGS. 1 through 9 show a relatively small number of individual cells within substrate 10, it should be understood that this is merely for purposes of illustration and explanation. In some embodiments of the invention, a device 100 will include many more such cells, resulting in the ability to present tactile information of greater quantity and/or finer granularity. For example, current manufacturing techniques allow individual cells to be spaced such that their centers are as close as 40 μm apart, resulting in over 400,000 cells per square inch of membrane surface 33. At this level of granularity, very complex information, including representations of the topology of an area and the shapes or contours of individual objects, including a human face, may be presented in tactile form.

Figure 10:
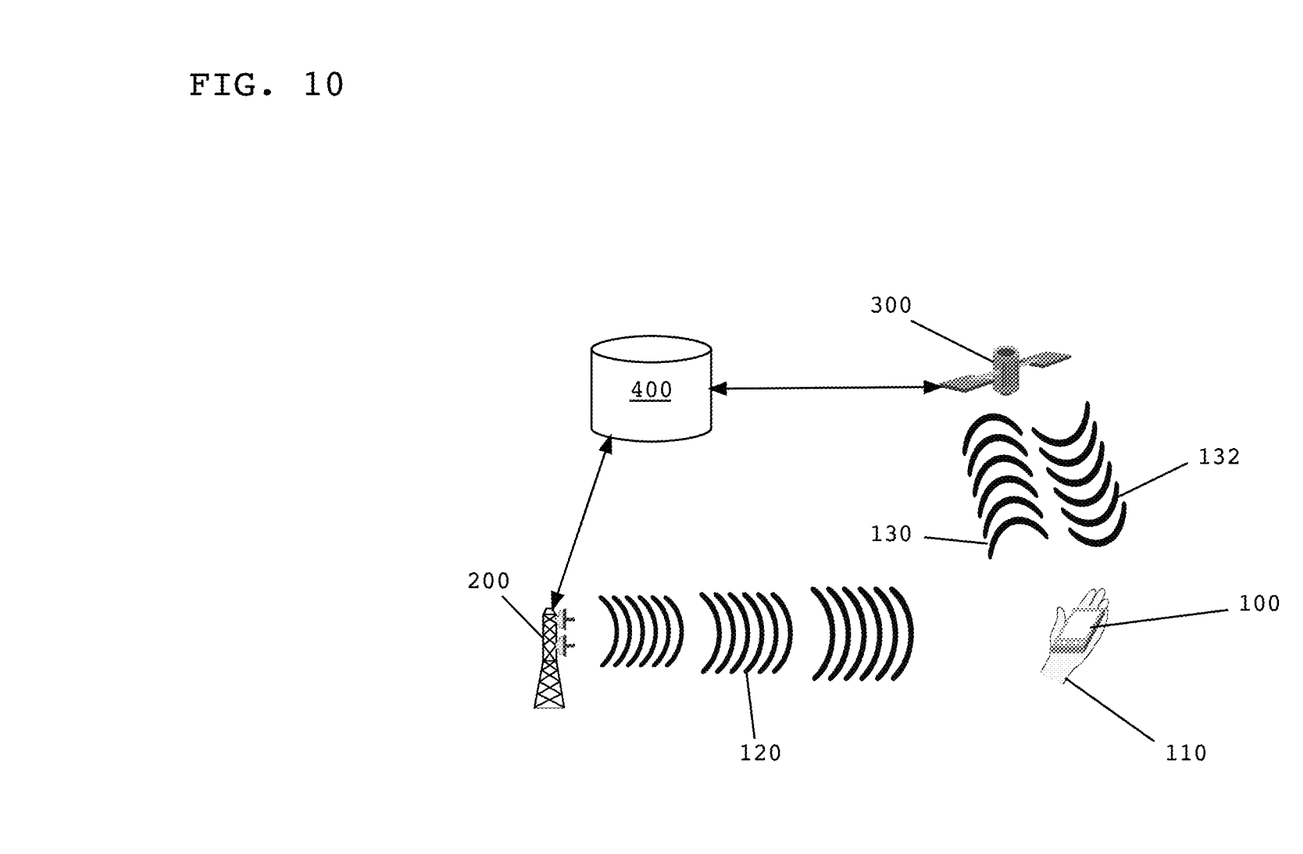
FIG. 10 shows a schematic view of a device according to an embodiment of the invention in communication with a transmitter and a global positioning system (GPS) satellite.

FIG. 10 shows a schematic view of device 100 in use by a user 110. As noted above, device 100 includes a receiver for receiving information capable of tactile presentation to user 110. Such information may, for example, be transmitted 120 from a transmitter 200. Transmitter 200 may include, for example, a cellular telephone system transmitter, an electronic mail delivery system, a radio transmitter, an Internet service provider (ISP) transmitter, etc. The information transmitted 120 may be stored in and retrieved from a database 400 or other storage medium accessible to transmitter 200.

Similarly, in some embodiments, device 100 may include a global positioning system (GPS) component capable of communication with at least one GPS satellite 300. In such embodiments, the GPS component is capable of transmitting 130 information to and/or receiving 132 information from GPS satellite 300. Such transmitted and/or received information may be used to determine a position of device 100 and/or other features, destinations, or points of interest, as well as their relative distance from device 100.

While device 100 is shown in FIG. 10 as a hand-held device, this is neither necessary nor essential. Although device 100 may be integrated into a cellular telephone, smart phone, tablet computer, laptop or notebook computer, device 100 may also function as a stand-alone device, whether handheld or otherwise. For example, device 100 may be incorporated into a device otherwise used by visually impaired users, such as a cane. Device 100 could, for example, be incorporated into a handle of a cane, such that, while the user uses the cane in its normal fashion, information may be presented to the user in tactile form through the handle. Device 100 may, of course, be incorporated into other devices, as will be apparent to one skilled in the art.

The terminology used herein is for the purpose of describing particular embodiments only and is not intended to be limiting of the disclosure. As used herein, the singular forms "a", "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A device for providing information to a user, the device comprising:
   a plurality of individually-addressable cells, each cell including an electrically-active material capable of changing shape and/or position in response to an electrical current;
   a electrical network connected to, and capable of delivering the electrical current to, each of the plurality of individually-addressable cells;
   a membrane atop the plurality of individually-addressable cells and in contact with the electrically-active material, onto which the change in shape and/or position of the electrically-active material in each cell may be transferred; and
   a receiver for receiving information capable of tactile presentation to a user using the plurality of individually-addressable cells,
   wherein each of the plurality of individually-addressable cells is independently capable of a range of changes in shape and/or position, such that the membrane may adopt a cross-sectional shape having a plurality of heights, the plurality of heights including a first height equal to an unraised surface of the membrane, a second height a first distance above the unraised surface of the membrane, and a third height a second distance above the unraised surface of the membrane, the second distance being greater than the first distance, and
   wherein each of the individually-addressable cells is encased in a fluid support material within the substrate.

2. The device of claim 1, wherein the plurality of individually-addressable cells is arranged in an array.

3. The device of claim 2, wherein the plurality of individually-addressable cells is capable of presenting the information in a Braille system.

4. The device of claim 1, wherein the plurality of individually-addressable cells is capable of presenting the information as a navigational symbol.

5. The device of claim 1, wherein each cell further includes an oil.

6. The device of claim 1, wherein the electrically-active material includes an alloy of samarium and cobalt.

7. The device of claim 1, wherein the membrane includes a silicone material.

8. The device of claim 1, further comprising:
   a global positioning system (GPS) component for determining a position of the device.

9. The device of claim 1, wherein the receiver is capable of receiving information in at least one format selected from a group consisting of: a text message, an electronic mail message, a voicemail message, and a navigational instruction.

10. A system for providing information to a user, the system comprising:
    a device including:
    a plurality of individually-addressable cells, each cell including an electrically-active material capable of changing shape and/or position in response to an electrical current;
    a electrical network connected to, and capable of delivering the electrical current to, each of the plurality of individually-addressable cells;
    a membrane atop the plurality of individually-addressable cells and in contact with the electrically-active material, onto which the change in shape and/or position of the electrically-active material in each cell may be transferred; and
    a receiver for receiving information capable of tactile presentation to a user using the plurality of individually-addressable cells; and
    a transmitter for transmitting to the device the information capable of tactile presentation,
    wherein each of the plurality of individually-addressable cells is independently capable of a range of changes in shape and/or position, such that the membrane may adopt a cross-sectional shape having a plurality of heights, the plurality of heights including a first height equal to an unraised surface of the membrane, a second height a first distance above the unraised surface of the membrane, and a third height a second distance above the unraised surface of the membrane, the second distance being greater than the first distance, and
    wherein each of the individually-addressable cells is encased in a fluid support material within the substrate.

11. The system of claim 10, wherein the transmitter is selected from a group consisting of: a cellular telephone system transmitter, an electronic mail delivery system, a radio transmitter, and an Internet service provider (ISP) transmitter.

12. The system of claim 10, wherein the transmitter includes a GPS transmitter.

13. The system of claim 10, wherein the plurality of individually-addressable cells is capable of presenting the information in a Braille system.

14. The system of claim 10, wherein the plurality of individually-addressable cells is capable of presenting the information as a navigational symbol.

15. The system of claim 10, wherein the electrically-active material includes an alloy of samarium and cobalt.

16. The system of claim 10, wherein the membrane includes a silicone material.

17. The system of claim 10, wherein the receiver is capable of receiving information in at least one format selected from a group consisting of: a text message, an electronic mail message, a voicemail message, and a navigational instruction.

18. A device for providing information to a user, the device comprising:
    a plurality of individually-addressable cells, each cell including an electrically-active oil capable of changing shape in response to an electrical current; and
    a membrane directly atop the plurality of individually-addressable cells and in contact with the electrically-active oil, onto a first surface adjacent the plurality of individually-addressable cells the change in shape of the electrically-active oil in each cell may be transferred and onto a second surface opposite the first surface the change in shape of the electrically-active oil is displayed,
    wherein each of the individually-addressable cells is encased in a fluid support material within the substrate.

* * * * *